United States Patent [19]

Cobb

[11] 4,048,209

[45] Sept. 13, 1977

[54] ISOMERIZATION OF THE CIS, TRANS ISOMERS OF 1,2,5,6-TETRASUBSTITUTED-1,5-CYCLOOCTADIENES TO THE CORRESPONDING CIS, CIS-ISOMERS

[75] Inventor: Raymond L. Cobb, Bartlesville, Okla.

[73] Assignee: Phillips Petroleum Company, Bartlesville, Okla.

[21] Appl. No.: 722,915

[22] Filed: Sept. 13, 1976

Related U.S. Application Data

[63] Continuation-in-part of Ser. No. 642,097, Dec. 18, 1975, abandoned.

[51] Int. Cl.$^2$ .................... C07C 121/48; C07C 69/74; C07C 61/26; C07C 103/19
[52] U.S. Cl. .................................... 260/464; 560/125; 560/127; 260/544 L; 260/557 R
[58] Field of Search ............... 260/464, 468 K, 544 L, 260/514 K, 557 R

[56] References Cited

U.S. PATENT DOCUMENTS 3,839,365   10/1974   Schmidt et al. .................. 260/346.3

OTHER PUBLICATIONS

Belluš, et al.; J.A.C.S., 96, pp. 5007–5009 (1974).
Schmidt et al.; C.A., 74, 42010m (1971).
Eliel, Stereochemistry of Carbon Compounds, (1972), pp. 341–346.

Primary Examiner—Joseph P. Brust

[57] ABSTRACT

Isomerization of the cis,trans isomers of 1,2,5,6-tetrasubstituted-1,5-cyclooctadienes to the corresponding cis,cis-isomers is carried out by contacting the cis,trans isomers with a halogen promoter in the presence of a suitable solvent in the absence of light.

6 Claims, No Drawings

ISOMERIZATION OF THE CIS, TRANS ISOMERS OF 1,2,5,6-TETRASUBSTITUTED-1,5-CYCLOOCTADIENES TO THE CORRESPONDING CIS, CIS-ISOMERS

This is a continuation-in-part of application Ser. No. 642,097, filed Dec. 18, 1975, now abandoned.

This invention relates to the isomerization of cyclooctadiene compounds.

The cis,cis- and cis,trans-isomers of 1,2,5,6-tetrasubstituted-1,5-cyclooctadienes are valuable starting materials for various syntheses. For example, the cis, cis-isomer can be used as an intermediate in the preparation of the 1,2,5,6-tetracarboxylic dianhydride. The cis,trans-isomers can be prepared by thermal cleavage of tricyclo[4.2.0.0$^{2,5}$]octanes. The tetranitrile-substituted compound, tricyclo[4.2.0.0$^{2,5}$]octane-1,2,5,6-tetracarbonitrile, cleaves at about 105° C to give cis,trans-1,5-cyclooctadiene-1,2,5,6-tetracarbonitrile. This tetranitrile-substituted cis,trans-isomer can be thermally isomerized to the corresponding cis,cis-isomer, cis,cis-1,5-cyclooctadiene-1,2,5,6-tetracarbonitrile, by heating to about 270° C. The yield of the cis,cis-isomer prepared by such thermal isomerization has been reported as 78 percent. It would be desirable to carry out the isomerization of the cis,trans-isomer to the cis,cis-isomer at a lower temperature and in greater yield.

Accordingly, it is an object of the present invention to provide a process for the isomerization of the cis,trans-isomer of 1,2,5,6-tetrasubstituted-1,5-cyclooctadiene to the corresponding cis,cis-isomer.

Other objects, aspects and advantages of this invention will be readily apparent to those skilled in the art from the reading of the following disclosure.

I have now discovered that the isomerization of the cis,trans-isomer of a 1,2,5,6-tetrasubstituted-1,5-cyclooctadiene to the corresponding cis,cis-isomer can be effected by contacting the cis,trans-isomer with a halogen promoter in the presence of a suitable solvent in the absence of light.

The process of the present invention can be represented as follows:

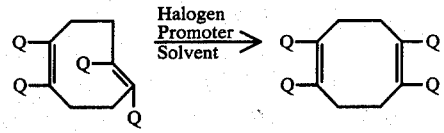

wherein each Q is selected from the group consisting of —CN, —COOR, —COX and —CONR$_2$, wherein R is selected from the group consisting of —H, or an alkyl group of 1 to 4 carbon atoms and X is Cl or Br.

Suitable feedstocks for use in the present process include cis,trans-1,5-cyclooctadiene-1,2,5,6-tetracarbonitrile; cis,trans-1,5-cyclooctadiene-1,2,5,6-tetracarboxylic acid; cis,trans-1,5-cyclooctadiene-1,2,5,6-tetracarboxamide; cis,trans-1,5-cyclooctadiene-1,2,5,6-tetracarbonyl tetrachloride; tetramethyl cis,trans-1,5-cyclooctadiene-1,2,5,6-tetracarboxylate; dimethyl trans-5,6-dicyano-1,5-cyclooctadiene-cis-1,2-dicarboxylate; 5,6-trans-bis-methoxycarbonyl-1,5-cyclooctadiene-cis-1,2-dicarboxamide; 5,6-trans-dicyano-1,5-cyclooctadiene-1,2-cis-dicarboxamide, and the like.

The halogen promoter is selected from the group consisting of chlorine, bromine or iodine. The halogen promoter is employed in an amount which will bring about the desired isomerization. In general, this amount will be in the range of 0.00001 to 1 mole of halogen promoter per mole of the cis,trans-isomer, preferably from 0.1 to 100 millimole of halogen on the same basis.

The solvent should function as a solvent under the conditions of isomerization. Suitable solvents include aromatic compounds such as benzene, toluene, the xylenes and the like; ethers such as tetrahydrofuran, diethyl ether, and the like, nitriles such as acetonitrile, propionitrile, benzonitrile and the like; lower alcohols such as methanol, ethanol, butanol and the like; esters such as ethyl acetate, methyl benzoate and the like; halogenated compounds such as carbon tetrachloride, chloroform, methylene chloride, 1,1,2-trichloro-1,2,2-trifluoroethane and the like; sulfolane; N,N-dimethylformamide; and low molecular weight carboxylic acids such as acetic acid, propionic acid and the like.

The isomerization process of this invention can be carried out over a broad range of temperature. In general, the process can be carried out at a temperature in the range of −50° to 100° C, preferably from 20° to 85° C. It will be appreciated that the selection of solvent and isomerization temperature are interdependent, e.g., benzene solidifies at about 5° C and would not be chosen as the solvent if it was desired to practice the invention at the lower end of the broad temperature range, e.g., −10° C.

The isomerization process is carried out for a time sufficient to isomerize substantially all of the cis,trans-isomer to the cis,cis-isomer. In general, the time required will be in the range of 0.1 to 24 hours.

The isomerization process of this invention can be carried out in the absence or presence of light.

In one embodiment of the present invention, the 1,2,5,6-tetrasubstituted cis,trans-1,5-cyclooctadienes are generated and isomerized in situ to the corresponding cis,cis-isomers. As discussed previously, for example, cis,trans-1,5-cyclooctadiene-1,2,5,6-tetracarbonitrile can be prepared by thermal cleavage of tricyclo[4.2.0.0$^{2,5}$]octane-1,2,5,6-tetracarbonitrile. By carrying out this cleavage in a suitable solvent, such as benzene, it becomes unnecessary to separate and isolate the cis,trans-isomer prior to isomerization to the cis,cis-isomer. Isomerization can be accomplished by adding the halogen promoter to the mixture of the cis,trans-isomer in the solvent. Alternatively, such cleavange and isomerization can be carried out simultaneously by adding the halogen promoter to the mixture of the tricyclooctane compound and solvent.

The cis,cis-isomer product of the process of this invention is a valuable intermediate in the preparation of the corresponding 1,2,5,6-tetracarboxylic dianhydride which is useful as an epoxy hardner and as a monomer for polymer production.

The following examples illustrate the invention:

EXAMPLE I

A solution of cis,trans-1,5-cyclooctadiene-1,2,5,6-tetracarbonitrile in refluxing benzene under a nitrogen atmosphere was stirred as a sollution of an equimolar quantity of bromine in benzene was added over a 90 minute period. The first few drops of the bromine solution appeared to be decolorized on addition but the bromine color soon persisted and a solid gradually began to separate from the stirred mixture. After all the bromine solution had been added, the refluxing mixture was stirred an additional hour and then filtered hot to give an essentially quantitative yield of cis,cis-1,5- cyclooctadiene-1,2,5,6-tetracarbonitrile as white crystals. Infrared and nuclear magnetic resonance spectral data indicated that the reaction product was cis,cis-1,5-cyclooctadiene-1,2,5,6-tetracarbonitrile.

Example I demonstrates the inventive process in refluxing benzene with a 1:1 molar ratio of halogen and cis,trans-tetranitrile feedstock.

Example II

A benzene solution of cis,trans-1,5-cyclooctadiene-1,2,5,6-tetracarbonitrile was prepared by dissolving the tetracarbonitrile in refluxing benzene and cooling the solution to room temperature. To this stirred benzene solution at room temperature, there was added all at once a solution of bromine in benzene. The bromine color persisted and a white material precipitated. The mixture was stirred an additional 14 hours at room temperature before filtering off an essentially quantitative yield of cis,cis-1,5-cyclooctadiene-1,2,5,6-tetracarbonitrile. The product identification was made on the basis of infrared and nuclear magnetic resonance spectral data.

Example II demonstrates the operability of the inventive system at room temperature. It is to be noted that essentially none of the known thermal isomerization of the cis,trans tetranitrile to the cis,cis-isomer took place in the boiling benzene.

EXAMPLE III

A benzene solution of cis,trans-1,5-cyclooctadiene-1,2,5,6-tetracarbonitrile was prepared as described in Example II. A benzene solution of iodine was prepared by dissolving a small crystal of $I_2$ benzene. The cis,trans-tetranitrile benzene solution was treated dropwise with a small portion of the iodine solution, and after about 2 hours an essentially quantitative yield of cis,cis-1,5-cyclooctadiene-1,2,5,6-tetracarbonitrile was removed by filtering the reaction mixture. The product was identified by infrared spectral analysis.

EXAMPLE IV

An acetonitrile solution of lithium bromide was prepared by contacting lithium bromide and acetonitrile. This solution was filtered and cis,trans-1,5-cyclooctadiene-1,2,5,6-tetracarbonitrile was added to the clear filtrate. This solution was stirred under a nitrogen atmosphere at room temperature as a solution of bromine in acetonitrile was added over a 60 minute period. The resulting golden orange solution was allowed to stand at room temperature overnight and then concentrated at reduced pressure to leave a solid. This solid residue was triturated with methylene chloride until it (the solid) was colorless. After the methylene chloride treatment, the remaining residue was completely soluble in water. The methylene chloride extract was concentrated at reduced pressure to give a solid-oil mixture. This material was partially soluble in tetrahydrofuran (THF) giving a THF solution and a THF-insoluble residue which exhibited an infrared spectrum characteristic of cis,cis-1,5-cyclooctadiene-1,2,5,6-tetracarbonitrile. The THF solution was concentrated to an oil which on treatment with diethyl ether gave additional cis,cis-isomer.

Example IV demonstrates that the cis,trans-1,5-cyclooctadiene-1,2,5,6-tetracarbonitrile is resistant to double bond bromination even in the presence of lithium bromide and bromine (a known double bond bromination system). The principal reaction which took place was the inventive halogen-promoted isomerization of the cis,trans-tetranitrile to the corresponding cis,cis-isomer.

EXAMPLE V

A mixture of tricyclo[4.2.0.0$^{2,5}$]octane-1,2,5,6-tetracarbonitrile and bromine in benzene was stirred at reflux for 72 hours and the bromine color persisted. The reaction mixture was filtered hot to give a solid consisting essentially of cis,cis-1,5-cyclooctadiene-1,2,5,6-tetracarbonitrile.

Example V demonstrates that the attempted bromination of tricyclo[4.2.0.0$^{2,5}$]octane-1,2,5,6-tetracarbonitrile in benzene also gave rise to cis,cis-1,5-cyclooctadiene-1,2,5,6-tetracarbonitrile. This transformation probably involves the in situ generation of cis,trans-1,5-cyclooctadiene-1,2,5,6-tetracarbonitrile and its subsequent halogen-promoted isomerization because in a separate run a sample of the tricyclo tetranitrile in boiling benzene gave rise to the cis,trans tetranitrile.

EXAMPLE VI

A mixture of tricyclo[4.2.0.0$^{2,5}$]octane-1,2,5,6-tetracarbonitrile in benzene was stirred under reflux for 20 hours to give complete solution. A small crystal of iodine was added to the hot solution and slow crystallization of a white solid began as the solution was allowed to cool. After standing at room temperature for 65 hours, the reaction mixture was filtered to remove a precipitate consisting essentially of cis,cis-1,5-cyclooctadiene-1,2,5,6-tetracarbonitrile. Concentration of the benzene mother liquor gave an additional amount of the cis,cis-isomer.

Example VI illustrates that the in situ generated cis,trans-1,5-cyclooctadiene-1,2,5,6-tetracarbonitrile from heating tricyclo[4.2.0.0$^{2,5}$]octane-1,2,5,6-tetracarbonitrile in boiling benzene followed by the addition of a small iodine crystal gives the cis,cis-isomer.

EXAMPLE VII

This example illustrates that the isomerization process of this invention can be carried out in the absence of light, as well as in the presence of light.

a. Preparation of a Benzene Solution of Cis,Trans-1,5-Cyclooctadiene-1,2,5,6-Tetracarbonitrile A 3.0 g sample of tricyclo[4.2.0.0$^{2,5}$]octane-1,2,5,6-tetracarbonitrile was placed in 150 ml benzene and the stirred reaction mixture was refluxed under a nitrogen blanket for 42 hours. Filtration of the hot solution gave 0.11 g of cis,cis-1,5-cyclooctadiene-1,2,5,6-tetracarbonitrile (verified by infrared spectrum). The filtrate (ca. 188 g) was separated into four aliquots of about 45 g each. Thus, each aliquot contained about 0.69 g of cis,trans-1,5-cyclooctadiene-1,2,5,6-tetracarbonitrile:

$$\frac{(3.00 - 0.11)}{4} \times \frac{(4 \times 45)}{188} =$$

0.69 g (3.33 mmols) cis, trans isomer b. Preparation of a Benzene Solution of Bromine 9.1 weight percent solution of bromine in benzene was prepared by adding 1.00 g of bromine to 10.00 g of benzene. A 1.5 ml portion of this solution delivered by syringe weighed 1.45 g. Thus, 1.5 ml portions of this solution contain 0.13 g (0.82 mmol) bromine.

c. Isomerization in the Absence of Light

A 45 g aliquot of the above benzene solution of cis,-trans-1,5-cyclooctadiene-1,2,5,6-tetracarbonitrile was placed in a 100 ml Pyrex flask equipped with a rubber septum and the entire apparatus was completely covered with aluminum foil to prevent the transmission of light to the reaction solution. A 1.5 ml aliquot of the bromine solution was added by syringe and the mixture was allowed to stand at room temperature for 3 days and then refrigerated for a few days before work-up. The supernatant was removed by means of a syringe without disturbing the aluminum foil wrapping, and the bulk of the product was washed out with benzene and filtered to give 0.83 g of a white solid identified as cis,-cis-1,5-cyclooctadiene-1,2,5,6-tetracarbonitrile based on an infrared spectrum.

d. Isomerization in the Presence of Light

A 45 aliquot of the above benzene solution of cis,-trans-1,5-cyclooctadiene-1,2,5,6-tetracarbonitrile was placed in a 100 ml Pyrex flask and a 1.5 ml aliquot of the bromine solution was added by syringe. The bromine color rapidly disappeared and the mixture became turbid due to the appearance of a white solid. The reaction mixture was allowed to stand at room temperature for 3 days and then refrigerated for a few days before work-up. Filtration gave 0.81 g of a white solid identified as cis,cis-1,5-cyclooctadiene-1,2,5,6-tetracarbonitrile based on an infrared spectrum.

Reasonable variations and modifications, which will be apparent to those skilled in the art, can be made in this invention without departing from the spirit and scope thereof.

What is claimed is:
1. A process for the production of a 1,2,5,6-tetrasubstituted-cis,cis-1,5-cyclooctadiene of the formula

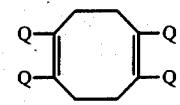

wherein each Q is individually selected from the group consisting of —CN, —COOH, —CONH$_2$, —COX and —COOR, wherein R is an alkyl group having from 1 to 4 carbon atoms and X is selected from the group consisting of Cl and Br, which comprises isomerizing the corresponding 1,2,5,6-tetrasubstituted-cis,trans-1,5-cyclooctadiene in the presence of an isomerization promoting amount of a halogen promoter selected from the group consisting of chlorine, bromine and iodine, at a temperature in the range of −50° to 100° C, for a time sufficient to effect said isomerization, in the absence of light.

2. The process of claim 1 wherein the amount of said halogen promoter is in the approximate range of 0.00001 to 1 mole of said halogen promoter per mole of said cis,trans-isomer.

3. The process of claim 1 wherein said Q is —CN.

4. The process of claim 1 wherein said 1,2,5,6-tetrasubstituted-cis,trans-1,5-cyclooctadiene is generated in situ by the thermal cleavage of the corresponding tricyclo-1,2,5,6-tetrasubstituted [4.2.0.0$^{2,5}$]octane.

5. The process of claim 1 wherein said halogen promoter is elemental iodine.

6. The process of claim 1 wherein said halogen promoter is bromine.